United States Patent
Nishihira et al.

[11] Patent Number: 5,514,829
[45] Date of Patent: May 7, 1996

[54] PROCESS FOR CONTINUOUSLY PRODUCING DIMETHYL CARBONATE

[75] Inventors: Keigo Nishihira; Shinichi Yoshida; Shuji Tanaka, all of Ube, Japan

[73] Assignee: Ube Industries, Ltd., Yamaguchi, Japan

[21] Appl. No.: 344,724

[22] Filed: Nov. 23, 1994

[30] Foreign Application Priority Data

Nov. 26, 1993 [JP] Japan .................................. 5-296277

[51] Int. Cl.$^6$ .................................................. C07C 68/00
[52] U.S. Cl. .................................................. 558/277
[58] Field of Search ............................................. 558/277

[56] References Cited

U.S. PATENT DOCUMENTS

| | | | |
|---|---|---|---|
| 4,879,401 | 11/1989 | Doumaux, Jr. et al. | 558/188 |
| 5,162,563 | 11/1992 | Nishihira et al. | 558/260 |
| 5,214,185 | 5/1993 | Nishihira et al. | 558/277 |

*Primary Examiner*—Johann Richter
*Assistant Examiner*—Michael G. Ambrose
*Attorney, Agent, or Firm*—Burgess, Ryan & Wayne

[57] ABSTRACT

A process for producing dimethyl carbonate is carried out by a first step of catalytically reacting carbon monoxide with methyl nitrite to produce dimethyl carbonate; a second step of absorbing dimethyl carbonate contained in a gas fraction withdrawn from the first step by dimethyl oxalate; a third step of regenerating methyl nitrite by contacting nitrogen monoxide contained in a gas fraction withdrawn from the second step with a molecular oxygen-containing gas and methyl alcohol; a fourth step of collecting dimethyl carbonate by distilling a liquid fraction withdrawn from the second step; and a fifth step of recovering methyl nitrite from a purge gas consisting of a portion of a regenerated gas fraction withdrawn from the third step by absorbing methyl nitrite in the purge gas by methyl alcohol to provide a methyl nitrite-containing liquid fraction and a nitrogen monoxide-containing gas fraction and bringing the gas fraction into contact with a molecular oxygen and methyl alcohol, to convert nitrogen monoxide in the gas fraction to methyl nitrite and to absorb this methyl nitrite by methyl alcohol, whereby methyl nitrite and nitrogen monoxide in the purge gas is recovered and reused with a high efficiency at a high level of safety.

16 Claims, 2 Drawing Sheets

5,514,829

PROCESS FOR CONTINUOUSLY PRODUCING DIMETHYL CARBONATE

BACKGROUND OF THE INVENTION

1. Field of the Invention

The present invention relates to a process for continuously producing dimethyl carbonate. More particularly, the present invention relates to an industrial process for continuously producing dimethyl carbonate by a catalytical reaction in gas phase of carbon monoxide with methyl nitrite in the presence of a solid catalyst, while effectively and safely recovering methyl nitrite and nitrogen monoxide from a purge gas withdrawn from a gas system circulating through a reaction system, and recycling the recovered methyl nitrite and nitrogen monoxide to the production of dimethyl carbonate.

Dimethyl carbonate is a compound useful as a material for synthesizing aromatic polycarbonates, medicines and agricultural chemicals, and as a solvent.

2. Description of the Related Art

A conventional industrial process for producing dimethyl carbonate by a catalytical reaction in gas phase of carbon monoxide with methyl nitrite in the presence of a solid catalyst comprises, as disclosed in U.S. Pat. No. 5,214,185, a first step of catalytically reacting carbon monoxide with methyl nitrite in gas phase in the presence of a solid catalyst in a reactor to produce dimethyl carbonate; a second step of absorbing dimethyl carbonate produced in the first step by an absorbing medium consisting of dimethyl oxalate in a dimethyl carbonate-absorbing column (absorbing column), to provide a liquid fraction comprising dimethyl carbonate absorbed by dimethyl oxalate and a non-condensed gas fraction containing nitrogen monoxide; a third step of regenerating methyl nitrite by bringing nitrogen monoxide in the non-condensed gas fraction into contact with molecular oxygen and methyl alcohol in a methyl nitrite-regenerating column (regenerating column); and a fourth step of distil-collecting dimethyl carbonate from the liquid fraction produced in the second step and containing dimethyl oxalate in which dimethyl carbonate is absorbed, in an extract-distilling column and a dimethyl carbonate-distilling column.

In the above-mentioned process, a gas containing carbon monoxide and methyl nitrite circulate through the first step, the second step and the third step. This circulating gas further contains a carbon dioxide gas which is produced as a by-product of the gas phase catalytical reaction of the first step, and an inert gas, for example, nitrogen gas, which is introduced into the circulating gas by accompanying with a NOx gas which is fed into the regenerating column to synthesize methyl nitrite. Therefore, to avoid the accumulation of the above-mentioned gases into high concentrations in the circulating gas, a portion of the circulating gas is continuously purged, as a purge gas, from the gas-circulating system.

The purge gas contains high contents of methyl nitrite and nitrogen monoxide, therefore, methyl nitrite and nitrogen monoxide are recovered from the purge gas.

For the purpose of recovery, for example, U.S. Pat. No. 4,879,401, discloses a recovering method in which a purge gas collected from a methyl nitrite-regenerating step is brought into contact with a molecular oxygen-containing gas and methyl alcohol to regenerate methyl nitrite from nitrogen monoxide contained in the purge gas and absorb the regenerated methyl nitrite together with methyl nitrite contained in the purge gas by methyl alcohol; and the resultant methyl alcohol solution containing methyl nitrite is recycled to the methyl nitrite-regenerating step.

In the above-mentioned third step, the regeneration of methyl nitrite from nitrogen monoxide is applied to only a portion of nitrogen monoxide contained in the circulating gas. However, in the above-mentioned recovering method, to recover and convert almost all nitrogen monoxide in the purge gas to methyl nitrite, the molecular oxygen-containing gas must be fed in a stoichiometric amount or more with respect to the amount of nitrogen monoxide, to the methyl nitrite-recovering step. This addition of the molecular oxygen-containing gas in an excessive amount causes, the resultant circulating gas to contain non-reacted molecular oxygen. Namely, the purge gas containing a high content of methyl nitrite is caused to further contain molecular oxygen gas. This purge gas has an increased risk of explosion. This problem must be solved. Also, since the methyl nitrile is regenerated from nitrogen monoxide in the purge gas which already has a high content of methyl nitrite, the total content of methyl nitrite in the purge gas increases to a level at which methyl nitrile in the purge gas cannot be fully absorbed by methyl alcohol. This problem, also, must be solved.

SUMMARY OF THE INVENTION

An object of the present invention is to provide a process for continuously producing dimethyl carbonate, while recovering and reusing methyl nitrite and nitrogen monoxide, which are useful components for the process of the invention, in a purge gas at a high safety with a high efficiency.

The above-mentioned object can be attained by the process of the present invention for continuously producing dimethyl carbonate, which comprises a first step of preparing dimethyl carbonate by a catalytic reaction of carbon monoxide with methyl nitrite in gas phase in the presence of a solid catalyst in a reactor;

a second step of absorbing the dimethyl carbonate by an absorption medium comprising dimethyl oxalate in a dimethyl carbonate-absorbing column, to provide an absorbing medium liquid fraction containing dimethyl carbonate and a non-condensed gas fraction containing nitrogen monoxide;

a third step of regenerating methyl nitrite by bringing the non-condensed gas fraction containing nitrogen monoxide into contact with molecular oxygen and methyl alcohol in a methyl nitrite-regenerating column, to provide a liquid fraction containing water dissolved in methyl alcohol and a regenerated gas fraction containing the regenerated methyl nitrite and nitrogen monoxide, a major portion of the regenerated gas fraction being recycled to the reactor of the first step;

a fourth step of collecting dimethyl carbonate by distilling the absorbing medium liquid fraction produced in the second step, in a distilling column; and a fifth step of recovering methyl nitrite from a purge gas consisting of a minor portion of the regenerated gas fraction produced in the third step and containing the regenerated methyl nitrite and nitrogen monoxide, (a) by bringing the purge gas into contact with methyl alcohol to provide a liquid fraction containing methyl nitrite absorbed by methyl alcohol, and a gas fraction containing nitrogen monoxide, and (b) by bringing the gas fraction containing nitrogen monoxide into contact with molecular oxygen and methyl alcohol to convert nitrogen monoxide to methyl nitrite and to provide a liquid fraction containing methyl nitrite absorbed by methyl alcohol.

DESCRIPTION OF THE PREFERRED EMBODIMENTS

Figure 1:
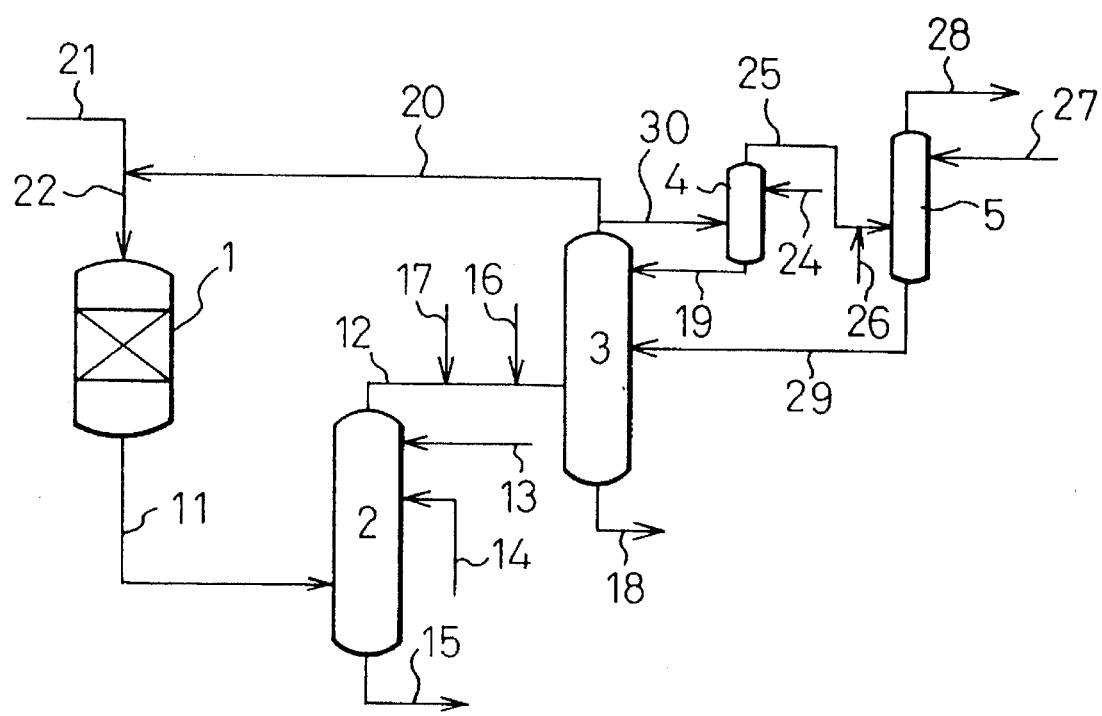
FIG. 1 is a flow sheet showing an embodiment of the process of the present invention.

The steps of the process of the present invention will be explained briefly below.

In the first step of the process of the present invention, a material gas containing carbon monoxide and methyl nitrite is introduced into a reactor packed with a solid catalyst in which a catalytical component consisting of a platinum group metal and/or a compound thereof and optionally an assistant catalytical component carried on a carrier, to cause carbon monoxide to react with methyl nitrite in gas phase and to provide a reaction product gas containing the resultant dimethyl carbonate.

In the second step of the process of the present invention, the reaction product gas provided in the first step is introduced into a dimethyl carbonate-absorbing column (which will be referred to as an absorbing column hereinafter) and brought into contact with an absorbing medium consisting of dimethyl oxalate to provide a non-condensed gas fraction containing nitrogen monoxide produced as a by-product of the catalytical reaction of the first step, and a liquid fraction separated from the non-condensed gas fraction, and comprising dimethyl oxalate, dimethyl carbonate absorbed by dimethyl oxalate and methyl alcohol.

In the third step, the non-condensed gas provided in the second step is introduced into a methyl nitrite-regenerating column, which will be referred to as a regenerating column hereinafter, and brought into contact with a molecular oxygen-containing gas and methyl alcohol which are also introduced into the regenerating column, to regenerate methyl nitrite from nitrogen monoxide in the non-condensed gas. The resultant regenerated gas fraction containing the regenerated methyl nitrite is recycled to the reactor for the first step.

In the fourth step, the dimethyl oxalate solution prepared in the second step and containing dimethyl carbonate and methyl alcohol is subjected to an extract-distilling procedure for removing methyl alcohol and then to a distilling procedure for collecting dimethyl carbonate.

In the above-mentioned first to fourth steps of the process of the present invention, a material gas comprising carbon monoxide and methyl nitrite is introduced into the reactor for the first step; a reaction product gas containing the resultant dimethyl carbonate is withdrawn from the reactor of the first step, and introduced into the absorbing column for the second step; a non-condensed gas which is separated from a dimethyl oxalate solution containing dimethyl carbonate and methyl alcohol, and containing nitrogen monoxide, is withdrawn from the absorbing column and introduced into the regenerating column for the third step, and a regenerated methyl nitrite-containing gas, which will be referred to as a regenerated gas, is withdrawn from the regenerating column.

The withdrawn regenerated gas is pressurized by a gas circulator located in a conduit line between the first step reactor and the third step regenerating column, recycled to the first step reactor and reused as a portion of the material gas in the first step reactor.

The circulating gas through the first, second and third steps contains a carbon dioxide gas produced as a by-product of the gas phase catalytic reaction in the first step, and an inert gas, for example, nitrogen gas, introduced as an accompanying gas together with a NOx gas for regenerating methyl nitrite into the regenerating column. To prevent the undesirable accumulation of the by-product gas and the inert gas in the circulating gas, a portion of the regenerated gas fraction is purged from a conduit located between the third step regenerating column and the gas-circulator.

The purged minor portion of the regenerated gas fraction will be referred to as a purge gas hereinafter.

In the fourth step of the process of the present invention, the dimethyl oxalate solution containing dimethyl carbonate and methyl alcohol and withdrawn from the second step absorbing column, is subjected to a collection of dimethyl carbonate by distillation.

In the fifth step of the process of the present invention, to effectively recover methyl nitrite and nitrogen monoxide from the purge gas, methyl alcohol is fed into a column for recovering methyl nitrite and brought into contact with the purge gas, before the methyl alcohol is fed into the regenerating column for the third step. In the methyl nitrite-recovering column, methyl nitrite contained in the purge gas is absorbed by and dissolved in methyl alcohol and recovered as a liquid fraction from the purge gas. The remained gas fraction in the methyl nitrite-recovering column contains nitrogen monoxide. This nitrogen monoxide-containing gas is withdrawn from the methyl nitrite-recovering column and introduced into a column for recovering nitrogen monoxide. In the nitrogen monoxide-recovering column, the nitrogen-monoxide-containing gas is brought into contact with molecular oxygen and methyl alcohol to convert nitrogen monoxide to methyl nitrite and dissolve the regenerated methyl nitrite in methyl alcohol. Since the nitrogen monoxide-containing gas withdrawn from the methyl nitrite-recovering column is substantially free from methyl nitrile, the contact of the nitrogen monoxide-containing gas with the molecular oxygen-containing gas is safely carried out without a risk of locally producing an explosive gas.

In a conventional process, the purge gas withdrawn from the third step regenerating column and containing methyl nitrite and nitrogen monoxide is directly fed into the nitrogen monoxide-recovering column. Namely, the contact of the purge gas with the molecular oxygen-containing is carried out in the presence of a certain amount of methyl nitrile and thus causes a high risk of explosion. Also, when methyl nitrile is regenerated from nitrogen monoxide in the nitrogen monoxide-recovering column, the resultant methyl nitrite causes an increase in the concentration of methyl nitrite. Therefore, the adsorption effect of methyl nitrite by methyl alcohol in the nitrogen monoxide-recovering column decreases.

In the fifth step of the process of the present invention, the purge gas is subjected firstly to a methyl nitrite-recovering procedure, and then to a nitrogen monoxide-recovering procedure. Therefore, methyl nitrite can be recovered with a high efficiency not only in the methyl nitrite-recovering procedure but also in the nitrogen monoxide-recovering procedure. A1 so, the nitrogen monoxide-recovering procedure can be effected without risk of explosion.

The first to fifth steps of the process of the present invention will be further explained in detail below.

First Step

In the first step of the process of the present invention, dimethyl carbonate is prepared by introducing a material gas containing carbon monoxide and methyl nitrite into a reactor packed with a solid catalyst comprising a catalytic platinum group metal element and/or compound and optionally an assistant catalytical component carried on a carrier, so as to catalytically react carbon monoxide with methyl nitrite in gas phase.

The solid catalyst usable for the process of the present invention may be selected from those disclosed in, for example, U.S. Pat. No. 5,162,563, comprising a catalytic component comprising at least one member selected from platinum group metal elements and compounds and optionally, an assistant catalytic component carried on a carrier.

The platinum group metal elements and compounds usable for the present invention may be selected from palladium, platinum, iridium, ruthenium and rhodium elements and compounds thereof. The most preferred metal compound is palladium chloride.

The solid catalyst may comprise an assistant catalytic component carried on the carrier and comprising at least one compound of other metals than the platinum group metals, for example, copper, iron, bismuth and cerium.

The carrier usable for the present invention comprises at least one member selected from, for example, activated carbon, alumina, silica, diatomaceous earth, zeolite and clay materials.

In the first step, carbon monoxide and methyl nitrite are usually diluted with an inert gas, for example, nitrogen gas or carbon dioxide gas which are inert to the catalytic reaction of the present invention, to provide a material gas. The material gas is fed to the reactor at a feeding rate suitable for causing the material gas to remain in contact with the solid catalyst preferably for a time of 10 seconds or less, more preferably 0.2 to 5 seconds. The reactor for containing the solid catalyst is preferably selected from single tube-type reactors and multi-table type reactors.

The concentration of methyl nitrite in the material gas is established in consideration of the reaction rate and safety. To obtain a satisfactory reaction rate, the concentration of methyl nitrite is preferably 1% by volume or more, more preferably 1 to 25% by volume. However, since methyl nitrite is an explosive compound, it is not preferred that the concentration of methyl nitrite be too high. Usually, in the process of the present invention, the preferable concentration of methyl nitrite in the material gas is 3 to 25% by volume.

The concentration of carbon monoxide in the material gas is broadly variable. However, in the continuous process of the present invention, since a portion of the circulating gas is purged as mentioned above, the increase in the concentration of carbon monoxide results in an increase in loss of carbon monoxide to the outside of the process system, and thus is not preferred in economical point of view. Accordingly, the industrially preferable concentration of carbon monoxide in the material gas is in the range of from 1 to 50% by volume, more preferably 5 to 30% by volume.

Usually, the catalytical reaction is carried out at a relatively low temperature, as long as the reaction rate at this temperature is satisfactory.

Preferably, the reaction temperature is in the range of from 50° to 200° C., more preferably from 80° to 150° C.

Also, the reaction pressure is preferably in the range of from the ambient atmospheric pressure (0 kg/cm$^2$G) to 10 kg/cm$^2$G, more preferably 1 to 6 kg/cm$^2$G.

After the catalytic reaction, a reaction product gas containing dimethyl carbonate, dimethyl oxalate, nitrogen monoxide, carbon dioxide, non-reacted carbon monoxide and methyl nitrite and an inert gas is delivered from the reactor.

The target dimethyl carbonate is collected by introducing the reaction product gas into an absorbing column for the second step, and absorbing dimethyl carbonate by dimethyl oxalate introduced into the absorbing column through an upper portion thereof.

Second step

In the second step, dimethyl carbonate in the reaction product gas is collected by bringing the reaction product gas into contact with an absorbing medium consisting of dimethyl oxalate, in an absorbing column.

In the absorbing column, the feeding rate of dimethyl oxalate is variable depending on the amount of dimethyl carbonate contained in the reaction product gas and introduced into the absorbing column. Usually, dimethyl oxalate is preferably fed in an amount of 3 to 10 times, more preferably 4 to 6 times the weight of dimethyl carbonate fed into the absorbing column.

To effect the absorption of dimethyl carbonate with a high efficiency, the absorbing temperature is preferably low. However, if the absorbing temperature is too low, dimethyl oxalate is solidified and the necessary energy consumption for the absorption disadvantageously increases. Therefore, the absorption is carried out at a temperature of 0° to 100° C., more preferably 30° to 80° C.

In the second step, an absorbing medium liquid fraction comprising dimethyl carbonate absorbed by dimethyl oxalate and a non-condensed gas fraction containing nitrogen monoxide are provided. The non-condensed gas fraction withdrawn from the absorbing column contains small amounts of dimethyl carbonate and dimethyl oxalate. If dimethyl carbonate and dimethyl oxalate are fed into the third step, they are uselessly consumed in the third step. Therefore, a small amount of methyl alcohol is preferably fed into the absorbing column (the second step) through a top portion of the absorbing column so that they are recovered by methyl alcohol. Usually, methyl alcohol is fed preferably in an amount of 5 to 30% by weight, more preferably 10 to 20% by weight based on the amount of dimethyl carbonate contained in the reaction product gas.

Since the non-condensed gas contains, in addition to non-reacted carbon monoxide and methyl nitrite, a large amount of nitrogen monoxide produced in the first step, this nitrogen monoxide is used to regenerate methyl nitrite in the regenerating column for the third step.

Third step

In the third step of the process of the present invention, methyl nitrite is regenerated by introducing the non-condensed gas into the regenerating column and bringing it into contact with a molecular oxygen-containing gas and methyl alcohol. The regenerating column is selected from packing columns, bubbling columns, spraying columns and tray columns which are usually employed as a gas-liquid contact reaction apparatus.

The molecular oxygen-containing gas usable for the process of the present invention may be a pure oxygen gas, a mixed gas consisting of oxygen diluted with an inert gas, for example, nitrogen gas, or air.

In the third step, the molecular oxygen-containing gas is fed in an amount of 0.08 to 0.2 mole in terms of oxygen per mole of nitrogen monoxide introduced into the regenerating column. The molecular oxygen-containing gas and the non-condensed gas containing nitrogen monoxide are brought into contact with methyl alcohol at a temperature of 60° C. or less for a contact time of 0.5 to 2 seconds.

In the third step, methyl alcohol is fed in a necessary amount or more to react with nitrogen dioxide produced from nitrogen monoxide and the molecular oxygen and with nitrogen monoxide in a substantially equimolar amount to that of nitrogen dioxide, and to completely absorb the regenerated methyl nitrite. Usually, methyl alcohol is fed preferably in an amount of 2 to 5 moles per mole of nitrogen monoxide contained in the gas fraction fed into the regenerating column.

In the process of the present invention, the methyl alcohol to be fed to the third step regenerating column is used in the fifth step, before being fed into the third step, to absorb methyl nitrite contained in the purge gas in a methyl nitrite-recovering column and a nitrogen monoxide-recovering column. Namely, in the third step, the methyl nitrite-containing methyl alcohol passed through the fifth step is fed into the regenerating column.

In the process of the present invention, methyl nitrite and nitrogen monoxide are lost by being absorbed by the absorbing medium in the absorbing column of the second step, by being dissolved in the liquid fraction in the regenerating column of the third step and by discharging in the fifth step. Therefore, the loss in the methyl nitrite is compensated by adding, methyl nitrite or a methyl nitrite-supply source, for example, a NOx gas, for example, nitrogen monoxide, nitrogen dioxide, dinitrogen trioxide and dinitrogen tetraoxide, and nitric acid, preferably, the NOx gas is fed into the regenerating column of the third step.

From the third step regenerating column, a liquid fraction is discharged. This liquid fraction comprises methyl alcohol containing water produced as a by-product of the regenerating reaction of methyl nitrite. The liquid fraction is subjected to a refining procedure of methyl alcohol by removing water. In this refining procedure, the content of water is reduced to a level of 2% by volume or less, preferably 0.2% by volume or less. The refined methyl alcohol is reused for the second, third and fifth steps.

Fourth step

The liquid fraction withdrawn from the second step absorbing column and containing the target dimethyl carbonate dissolved in dimethyl oxalate is subjected to a fourth step to collect the target dimethyl carbonate.

In the fourth step, impurities having a low boiling temperature, for example, methyl alcohol and a small amount of methyl formate which is a by-product of the catalytic reaction, are removed by an extract-distilling procedure, and then the target dimethyl carbonate is collected by a distilling procedure.

Fifth step a) Recovery of methyl nitrite

The recovery of methyl nitrite in the fifth step of the process of the present invention is carried out by bringing a purge gas into contact with methyl alcohol, before the methyl alcohol is fed into the third step regenerating column, in a methyl nitrite-recovering column. The purge gas consists of a portion of the regenerated gas fraction discharged from the third step regeneration column.

During the contact of the purge gas with methyl alcohol, methyl nitrite contained in the purge gas is absorbed and dissolved in methyl alcohol, and a liquid fraction comprising the methyl alcohol solution of methyl nitrite and a gas fraction separated from the liquid fraction and containing nitrogen monoxide are provided.

The methyl nitrite containing methyl alcohol solution is recycled to the third step regenerating column. Also, the nitrogen monoxide-containing gas fraction is fed into a nitrogen monoxide-recovering column.

The apparatus for contacting the purge gas with methyl alcohol, namely the methyl nitrite-recovering column does not need to be a specific apparatus and may be selected from conventional gas-liquid contact type absorbing apparatuses, for example, packing columns, tray column, and bubbling columns. The methyl nitrite-recovering column is arranged between a location at which the purge gas is withdrawn from the gas-circulating conduit system and a location at which the molecular oxygen-containing gas is mixed into the nitrogen monoxide-containing gas fraction. Where the purge gas is directly withdrawn from the top portion of the third step regenerating column, the methyl nitrite-recovering column may be directly attached to the top portion of the third step regenerating column.

The contact of the purge gas with methyl alcohol is carried out to absorb methyl nitrite in the purge gas by methyl alcohol. Therefore, it is preferable that the contact of the purge gas with methyl alcohol be carried out at a low temperature. However, since methyl alcohol is supplied in a large amount excessive to absorb methyl nitrite from the purge gas, the contacting temperature does not need to be very low. Preferably, the contacting temperature is in the range of from −5° C. to 30° C. As mentioned above, the liquid fraction discharged from the methyl nitrite-recovering column and containing a solution of methyl nitrite in methyl alcohol is fed into the methyl nitrite-regenerating column for the third step. Therefore, the amount of methyl alcohol fed into the methyl nitrite-recovering column for the fifth step is similar to that fed into the methyl nitrite-regenerating column for the third step. Usually, the amount of methyl alcohol fed into the stage (a) of the fifth step methyl nitrite-recovering column is 2 to 5 moles per mole of nitrogen monoxide contained in the gas fraction fed into the third step methyl nitrite-regenerating column.

As mentioned above, the purge gas consists of a portion of the regenerated gas fraction withdrawn from the third step methyl nitrite-regenerating column. The amount of the purge gas is variable depending on the amounts of the by-product gas, for example, carbon dioxide gas and the inert gas, for example nitrogen gas, accumulated in the gas circulating through the first to third steps. Usually, the amount of the purge gas is controlled to a level not less than the amount of the inert gas, for example, nitrogen gas, introduced together with the NOx gas into the third step.

Preferably, the purge gas is in an amount of 0.1 to 30%/hr based on the amount of the regenerated gas fraction withdrawn from the third step methyl nitrite-regenerating column.

b) Recovery of nitrogen monoxide

In the methyl nitrite-recovering column, a liquid fraction comprising methyl nitrite absorbed by methyl alcohol and a gas fraction separated from the liquid fraction and containing nitrogen monoxide are provided.

The nitrogen monoxide-containing gas fraction is introduced into a nitrogen monoxide-recovering column and brought into contact with a molecular oxygen-containing gas and methyl alcohol. During the contact, nitrogen monoxide is converted to methyl nitrite, and the resultant methyl nitrite is absorbed by and dissolved in methyl alcohol. The methyl nitrite-containing methyl alcohol is recycled to the third step methyl nitrite-regenerating column.

The operational conditions of the nitrogen monoxide-recovering column are similar to those of the third step methyl nitrite-regenerating column, except that the molecular oxygen-containing gas is fed in an amount of 0.2 mole or more, in terms of oxygen, per mole of nitrogen monoxide contained in the purge gas, no NOx gas is fed, and methyl alcohol is directly fed into the nitrogen monoxide-recovering column without passing through the methyl nitrite-recovering column.

An embodiment of the process of the present invention will be explained next in detail with reference to FIG. 1 which is a flow sheet of the process of the present invention.

Referring to FIG. 1, a material gas comprising carbon monoxide, methyl nitrite and nitrogen monoxide is pressurized by a gas-circulator 1 (not shown in FIG. 1) located in a conduit line 20 and then introduced into a top portion of a multi-tube type reactor equipped with reaction tubes packed with a platinum group metal compound-containing solid catalyst, through a conduit 22. In this reactor 1, a catalytic reaction of carbon monoxide with methyl nitrite is carried out in the gas phase. A reaction product-containing gas passed through the catalyst layers in the reaction tubes is withdrawn from the bottom portion of the reactor 1 and then introduced into a dimethyl carbonate-absorbing column 2 through a conduit 11.

In the absorbing column 2, the introduced gas containing dimethyl carbonate is brought into contact with methyl alcohol introduced through a conduit 13 and with dimethyl oxalate introduced through a conduit 14, and dimethyl carbonate in the introduced gas is absorbed and collected by dimethyl oxalate. A resultant liquid fraction containing dimethyl carbonate, dimethyl oxalate and methyl alcohol is withdrawn from a bottom portion of the absorbing column through a conduit 15, and fed into a refining apparatus (not shown in FIG. 1) which may be a conventional apparatus, for example, a distilling column, for collecting dimethyl carbonate from the liquid fraction.

Also, a non-condensed gas fraction separated from the liquid fraction and containing non-reacted carbon monoxide, methyl nitrite and nitrogen monoxide produced, as a by-product, by the catalytic reaction is withdrawn from the top portion of the absorbing column 2 through a conduit 12.

In the conduit 12, the non-condensed gas is mixed with a molecular oxygen-containing gas introduced through a conduit 16, and the resultant mixed gas is introduced into a column 3 for regenerating methyl nitrite and brought into contact in counter current with methyl alcohol introduced into a top portion of the regenerating column 3 through a conduit 19. During the contact, methyl nitrite is regenerated in the column 3. If the amount of nitrogen source necessary to regenerate methyl nitrite is not much enough, a NOx gas is introduced in a necessary amount into the conduit 12 or the regenerating column 3 through a conduit 17, to mix with the non-condensed gas and the molecular oxygen-containing gas.

The resultant regenerated methyl nitrite-containing gas is withdrawn from a top portion of the regenerating column 3 through a conduit 20, and introduced together with fresh carbon monoxide fed through a conduit 21 into the reactor 1 through the conduct 22. A by-product produced in the regenerating column 3 and consisting of water is withdrawn in the state of a solution in methyl alcohol from the bottom portion of the regenerating column 3 through a conduit 18. The water-methyl alcohol solution is subjected to a procedure for removing water from the solution, for example, a distilling procedure. The recovered methyl alcohol is recycled into an absorbing column 2 through the conduit 13, into a methyl nitrate-recovering column 4 through a conduit 24 and/or into a nitrogen monoxide-recovering column 5 through a conduit 27, and re-used in each column.

A portion of the regenerated methyl nitrite-containing gas produced in and withdrawn from the regenerating column 3 is purged from the gas-recycling line and introduced into a column 4 for recovering methyl nitrite through a conduit 30. The purged portion of the regenerated methyl nitrite-containing gas will be referred to as a purge gas hereinafter.

In the methyl nitrite-recovering column 4, the introduced purge gas is brought into contact countercurrently with methyl alcohol introduced through the conduit 24 so that methyl nitrite in the purge gas is absorbed and recovered by methyl alcohol. A resultant solution of methyl nitrite in methyl alcohol is withdrawn from the bottom portion of the methyl nitrite-recovering column 4, and fed into the top portion of the methyl nitrite-regenerating column 3 through a conduit 19.

A remaining fraction of the purged gas from which methyl nitrile has been recovered in the methyl nitrite-recovering column 4, is withdrawn from the top portion of the column 4 through a conduit 25.

The gas fraction withdrawn from the methyl nitrite-recovering column 4 is mixed in the conduit 25 with a molecular oxygen-containing gas introduced through a conduit 26.

The mixed gas is introduced into a bottom portion of a column 5 for recovering nitrogen monoxide. In this nitrogen monoxide-recovering column 5, the mixed gas is brought into contact countercurrently with methyl alcohol introduced into a top portion of the nitrogen monoxide-recovering column 5, so that nitrogen monoxide and molecular oxygen contained in the mixed gas react with methyl alcohol and methyl nitrite is regenerated by the reaction and dissolved in methyl alcohol.

The resultant solution of methyl nitrite in methyl alcohol is withdrawn from the bottom portion of the nitrogen monoxide-recovering column 5 and recycled into a middle portion of the methyl nitrite-regenerating column 3 through a conduit 29.

A residual gas fraction in the nitrogen monoxide-recovering column 5 contains nitrogen gas and a small amount of a by-product gas and is discharged from a top portion of the nitrogen monoxide-recovering column 5 through a conduit 28.

EXAMPLES

The present invention will be further explained by the following specific examples.

In the examples, the space time yield (STY) in $kg/m^3 \cdot hr$ of dimethyl carbonate was calculated in accordance with the following equation (I):

$$STY\ (kg/m^3 \cdot hr) = a(b \times \theta) \qquad (I)$$

wherein $\theta$ represents a catalytic reaction time in hours of carbon monoxide with methyl nitrite in a reaction tube, a represents a weight in kg of the resultant dimethyl carbonate during the catalytic reaction time $\theta$, and b represents a volume in $m^3$ of a solid catalyst present in the reaction tube.

Example 1

A solid catalyst as disclosed in U.S. Pat. No. 5,162,563, in the form of pellets each having a diameter of 4 mm and a length of 6 mm and comprising palladium chloride and cupric chloride carried on a carrier consisting of activated carbon available under the trademark of Shirasagi from Takeda Yakuhin K.K., was packed in an amount of 1.71 liters into 6 reaction tubes having an inside diameter of 27 mm and a length (height) of 500 mm, in a multiple tube type reactor, to form catalyst layers. The reactor was equipped with a jacket through which hot water flows.

A material gas comprising 20.0% by volume of carbon monoxide, 10.0% by volume of methyl nitrite, 4.0% by volume of nitrogen monoxide, 7.0% by volume of methyl alcohol, 1.0% by volume of carbon dioxide, and 58.0% by volume of nitrogen was pre-heated at a temperature of about 90° C. in a heat exchanger, and then fed into a top portion of the reactor through a diaphragm type gas-circulating pump at a feeding rate of 6.80 $Nm^3$/hr under a pressure of 4.02 $kg/cm^2G$, so that the material gas was brought into contact with the solid catalyst layers in the reactor.

The temperature of the center portions of the catalyst layers was maintained at a level of about 120° C. by circulating hot water through the jacket arranged on the shell of the reactor, to catalytically react carbon monoxide with methyl nitrite.

In this reaction, the space time yield (STY) of dimethyl carbonate was 338 $kg/m^3 \cdot hr$.

The reaction product-containing gas passed through the catalyst layers was withdrawn from the reactor and introduced into a bottom portion of an absorbing column consisting of a Raschig ring packing type gas-liquid contact absorbing apparatus having an inside diameter of 100 mm and a length (height) of 1300 mm. Also, methyl alcohol was introduced at a feeding rate of 0.18 liter/hr into the top of the absorbing column and dimethyl oxalate was introduced into a middle portion of the absorbing column through an inlet located 200 mm below the top of the column at a feeding rate of 2.50 kg/hr, so that the reaction product-containing gas was brought into contact countercurrently with the introduced methyl alcohol and dimethyl oxalate at a column top, temperature of 35° C. and at a column bottom temperature of 55° C. As a result, a liquid fraction comprising 78.1% by weight of dimethyl oxalate, 16.8% by weight of dimethyl carbonate, 4.2% by weight of methyl alcohol and 0.1% by weight of methyl formate was obtained at a flow rate of 3.28 kg/hr from the bottom of the absorbing column.

Also, a non-condensed gas fraction was withdrawn at a flow rate of 6.64 $Nm^3$/hr from the top portion of the absorbing column. The withdrawn non-condensed gas contained methyl nitrite in a lower concentration than that in the material gas, because a portion of methyl nitrite contained in the material gas was consumed by the catalytic reaction with carbon monoxide in the reactor. The non-condensed gas was fed into a methyl nitrite-regenerating column to regenerate methyl nitrite from nitrogen monoxide contained in the non-condensed gas.

Also, since a portion of methyl nitrite introduced into the absorption column was dissolved in methyl alcohol and discharged together with the dimethyl carbonate absorbed by dimethyl oxalate, a NOx gas was fed into the regeneration column, to compensate the discharged methyl nitrite.

Namely, the non-condensed gas was mixed with 78N liter/hr of oxygen gas and 7.5N liter/hr of a gas containing 14.0% by volume of nitrogen monoxide, and the resultant mixed gas was introduced into the regenerating column consisting of a gas-liquid contact-absorbing apparatus having an inside diameter of 158 mm and a length (height) of 1400 mm. The introduced mixed gas was brought into contact in counter current with methyl alcohol introduced at a flow rate of 1.5 liter/hr into the top portion of the regenerating column through a methyl nitrite-recovering column, at a column top temperature of 30° C. and at a column bottom temperature of 40° C., to regenerate methyl nitrite.

In the regenerating column, a liquid fraction comprising a by-product consisting of water and dissolved in methyl alcohol and a gas fraction containing the regenerated methyl nitrite were provided.

The gas fraction was withdrawn at a flow rate of 6.66 $Nm^3$/hr from the top portion of the regenerating column, and comprised 17.5% by volume of carbon monoxide, 10.1% by volume of methyl nitrite, 4.0% by volume of nitrogen monoxide, 1.01% by volume of carbon dioxide and 60.4% by volume of nitrogen. A portion of the withdrawn gas fraction was purged in an amount of 6.5N liter/hr, as a purge gas, and the remaining portion of the withdrawn gas fraction was recycled into the reactor.

The purge gas was introduced into a bottom portion of a methyl nitrite-recovering column consisting of a gas-liquid contacting apparatus having an inside diameter of 18 mm and a length (height) of 250 mm, and brought into contact countercurrently with methyl alcohol cooled to a temperature of 10° C. and introduced in an amount of 1.5 liter/hr into a top portion of the methyl nitrite-recovering column, to absorb methyl nitrite contained in the purge gas by methyl alcohol. A resultant liquid fraction comprising a solution of methyl nitrite in methyl alcohol was withdrawn from the bottom portion of the methyl nitrite-recovering column and recycled into the top portion of the methyl nitrite-regenerating column. Also, a resultant gas fraction was withdrawn from the top portion of the methyl nitrite-recovering column and contained 0.2% by volume of methyl nitrite and 4.0% by volume of nitrogen monoxide. The withdrawn gas fraction was mixed with 1.0N. liter/hr of air and the mixed gas was fed into a nitrogen monoxide-recovering column.

Namely, the mixed gas was introduced into the bottom portion of the nitrogen monoxide-recovering column consisting of a gas-liquid contacting apparatus having an inside diameter of 27 mm and a length (height) of 300 mm, and brought into contact countercurrently with 0.2 liter/hr of methyl alcohol cooled to a temperature of 5° C. and introduced into the top portion of this column, to regenerate methyl nitrite from nitrogen monoxide contained in the purge gas. The regenerated methyl nitrite was absorbed by methyl alcohol.

The resultant liquid fraction contained 0.4% by weight of methyl nitrite dissolved in methyl alcohol, and recycled into a middle portion of the regenerating column. Also, the resultant gas fraction contained 200 ppm by volume of methyl nitrite and 50 ppm by volume of nitrogen monoxide and withdrawn from the top portion of the nitrogen monoxide-recovering column.

After withdrawing the purge gas, the remaining portion of the gas fraction produced in the regenerating column was mixed in an amount of 6.66 $Nm^3$/hr with 0.15 $Nm^3$/hr of carbon monoxide, and the mixed gas containing 20.0% by volume of carbon monoxide, 10.0% by volume of methyl nitrite, 4.0% by volume of nitrogen monoxide, 7.0% by volume of methyl alcohol, 1.0% by volume of carbon dioxide and 58.0% by volume of nitrogen was introduced as a material gas into the reactor.

The liquid fraction withdrawn from the regenerating column and containing 2.0% by weight of water dissolved in methyl alcohol was subjected in a flow rate of 1.7 liters/hr to a distillation to remove water, and then the resultant refined methyl alcohol was re-used as a methyl alcohol source for the absorbing column, the regenerating column, the methyl nitrite-recovering column and the nitrogen monoxide-recovering column.

The target dimethyl carbonate was continuously collected in an amount of 0.540 kg/hr by distilling the liquid fraction in an amount of 3.28 kg/hr withdrawn from the absorbing column. The results are shown in Table 1.

Comparative Example 1

The same procedures as in Example 1 were carried out with the following exceptions.

Figure 2:
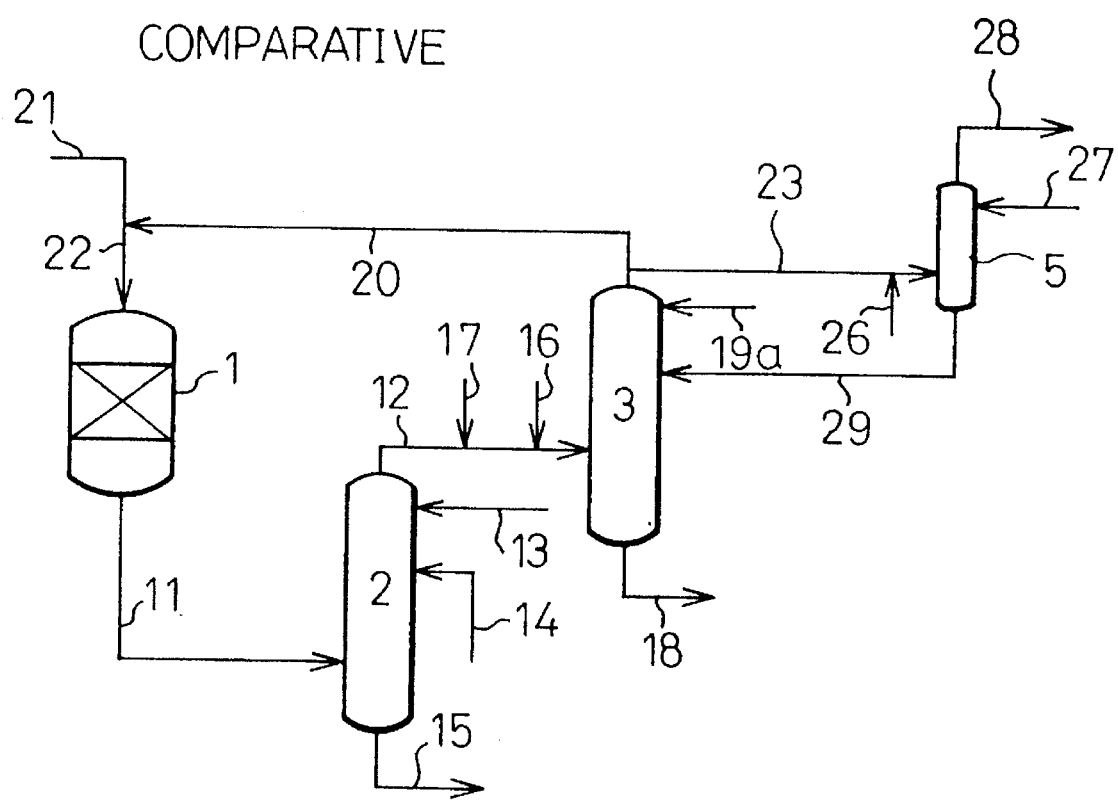
FIG. 2 is a flow sheet showing a comparative process to that of the present invention.

The process system shown in FIG. 1 was replaced by that shown in FIG. 2. The process system of FIG. 2 had no methyl nitrite-recovering column 4.

Referring to FIG. 2, in a reactor 1, dimethyl carbonate was prepared in a space time yield (STY) of 338 kg/m$^3$·hr. After the dimethyl carbonate was absorbed by dimethyl oxalate in an absorbing column 2, methyl nitrite was regenerated in a regenerating column 3. Methyl alcohol was directly fed into the regenerating column 3 through a conduit 19.

A portion of a gas fraction discharged from the top portion of the regenerating column 3 through a conduit 20 was withdrawn as a purge gas through a conduit 30a. The purge gas was mixed with 1.0N liter/hr of air fed through a conduit 26, and the mixed gas was introduced into the bottom portion of a nitrogen monoxide-recovering column 5 consisting of a gas-liquid contacting apparatus having an inside diameter of 27 mm and a length (height) of 300 mm. The introduced mixed gas was brought into contact countercurrently with 0.2 liter/hr of methyl alcohol cooled to a temperature of 5° C. and introduced into the top portion of the column 5, to absorb methyl nitrite contained in the purge gas by methyl alcohol, to convert nitrogen monoxide contained in the purge gas to methyl nitrite, and to absorb the regenerated methyl nitrite by methyl alcohol.

The resultant liquid fraction contained 1.3% by weight of methyl nitrite dissolved in methyl alcohol. This liquid fraction was withdrawn from the bottom portion of the column 5 and recycled to a middle portion of the regenerating column 3.

Also, the resultant gas fraction was withdrawn from the top portion of the column 5. This gas fraction contained 2000 ppm by volume of methyl nitrite and 80 ppm by volume of nitrogen monoxide.

The results are shown in Table 1. Table 1 shows contents of methyl nitrite and nitrogen monoxide contained in each of the purge gas, the gas fraction withdrawn from the methyl nitrite-recovering column, the gas fraction introduced into the nitrogen monoxide-recovering column, the gas fraction discharged from the nitrogen monoxide-recovering column and the liquid fraction withdrawn from the nitrogen monoxide-recovering column.

TABLE 1

| Item | | Example 1 | Comparative Example 1 |
|---|---|---|---|
| Purge gas | MN conc. (*)$_1$ (vl %) | 10.1 | 10.1 |
| | NO conc. (*)$_2$ (vl %) | 4.0 | 4.0 |
| Withdrawn gas fraction from MN-recovering column | MN conc. (vl %) | 0.2 | — |
| | NO conc. (vl %) | 4.0 | — |
| Introduced gas fraction into NO-recovering column | MN conc. (vl %) | 0.2 | 10.1 |
| | NO conc. (vl %) | 4.0 | 4.0 |
| Discharged gas fraction from No-recovering column | MN conc. (vl ppm) | 200 | 2000 |
| | NO conc. (vl ppm) | 50 | 80 |
| Withdrawn liquid fraction from NO-recovering column | MM conc. (wt %) | 0.4 | 1.3 |

Note:
(*)$_1$ . . . MN: Methyl nitrite
(*)$_2$ . . . NO: Nitrogen monoxide

Table 1 clearly shows that in the continuous process of the present invention for producing dimethyl carbonate by a catalytic reaction of carbon monoxide with methyl nitrite in the presence of a solid catalyst, methyl nitrite and nitrogen monoxide in the gas circulating system can be recovered with a high efficiency by applying a methyl nitrite-recovering procedure and a nitrogen monoxide-recovering procedure to a purge gas withdrawn from the gas circulating system.

Also, since methyl nitrite in the purge gas is selectively recovered by absorbing it by methyl alcohol so as to reduce the concentration of methyl nitrite in the purge gas, the absorbing step for methyl nitrite by methyl alcohol can be effected with an increased efficiency. Also, nitrogen monoxide in the purge gas can be substantially completely recovered by converting it to methyl nitrite and absorbing the resultant methyl nitrite by methyl alcohol. Further, after the concentration of methyl nitrite in the purge gas is reduced, the resultant gas fraction is mixed with an oxygen-containing gas which is necessary to regenerate methyl nitrite from nitrogen monoxide. Therefore, the mixed gas exhibits a significantly reduced risk of explosion. Accordingly, the process of the present invention is useful for continuously producing dimethyl carbonate at a high level of safety with an enhanced efficiency.

We claim:

1. A process for continuously producing dimethyl carbonate comprising:
   a first step of preparing dimethyl carbonate by a catalytic reaction of carbon monoxide with methyl nitrite in a gas phase in the presence of a solid catalyst in a reactor;
   a second step of absorbing the dimethyl carbonate by an absorption medium comprising dimethyl oxalate in a dimethyl carbonate-absorbing column, to provide an absorbing medium liquid fraction containing dimethyl carbonate and a non-condensed gas fraction containing nitrogen monoxide;
   a third step of regenerating methyl nitrite by bringing the non-condensed gas fraction containing nitrogen monoxide into contact with molecular oxygen and methyl alcohol in a methyl nitrite-regenerating column, to provide a liquid fraction containing water dissolved in methyl alcohol and a regenerated gas fraction containing the regenerated methyl nitrite and nitrogen monoxide, a major portion of the regenerated gas fraction being recycled to the reactor of the first step;

a fourth step of collecting dimethyl carbonate by distilling the absorbing medium liquid fraction produced in the second step, in a distilling column; and a fifth step of recovering methyl nitrite from a purge gas consisting of a minor portion of the regenerated gas fraction produced in the third step and containing the regenerated methyl nitrite and nitrogen monoxide, (a) by bringing the purge gas into contact with methyl alcohol in an amount of 2 to 5 moles per mole of nitrogen monoxide introduced into the methyl nitrite-regenerating column of the third step, at a contact temperature of −5° to 30° C., to provide a liquid fraction containing methyl nitrite absorbed by methyl alcohol and a gas fraction containing nitrogen monoxide, and (b) by bringing the gas fraction containing nitrogen monoxide into contact with molecular oxygen and methyl alcohol to convert nitrogen monoxide to methyl nitrite and to provide a liquid fraction containing methyl nitrite.

2. The process as claimed in claim 1, wherein the methyl nitrite containing liquid fraction produced in the stage (a) of the fifth step is recycled to the methyl nitrite-regenerating column of the third step.

3. The process as claimed in claim 1, wherein the solid catalyst for the first step comprises a catalytic component comprising at least one member selected from the group consisting of platinum group metal elements and compounds and a carrier for the catalytic component comprising at least one member selected from activated carbon, alumina, silica, diatomaceous earth, zeolite and clay minerals.

4. The process as claimed in claim 3, wherein the solid catalyst further comprises an assistant catalytic component comprising at least one member selected from the group consisting of copper compounds, iron compounds, bismuth compounds and cerium compounds.

5. The process as claimed in claim 1, wherein in the first step, carbon monoxide and methyl nitrite are diluted with an inert gas to form a feed gas, and in the feed gas, carbon monoxide is in a concentration of 1 to 50% by volume and methyl nitrite is in a concentration of 1 to 25% by volume.

6. The process as claimed in claim 1, wherein in the first step, the catalytic reaction is carried out at a temperature of 50° to 200° C. under a pressure of from 0 to 10 kg/cm$^2$G.

7. The process as claimed in claim 1, wherein in the second step 2, dimethyl oxalate is used in an amount of 3 to 10 times the weight of dimethyl carbonate introduced into the second step.

8. The process as claimed in claim 1, wherein the second step is carried out at a temperature of 0° to 100° C.

9. The process as claimed in claim 1, wherein in the second step, methyl alcohol is introduced into the dimethyl carbonate-absorbing column to recover dimethyl carbonate and dimethyl oxalate accompanying with the non-condensed gas, the introduced methyl alcohol being in an amount of 5 to 30% by weight based on the weight of dimethyl carbonate introduced into the dimethyl carbonate-absorbing column.

10. The process as claimed in claim 1, wherein in the third step, the molecular oxygen-containing gas contains molecular oxygen in an amount of 0.08 to 0.2 mole per mole of nitrogen monoxide introduced into the methyl nitrite-regenerating column.

11. The process as claimed in claim 1, wherein in the third step, the contact of the non-condensed gas with the molecular oxygen-containing gas and methyl alcohol is carried out at a temperature of 60° C. or less.

12. The process as claimed in claim 1, wherein in the third step, the introduced methyl alcohol is in an amount of 2 to 5 moles per mole of nitrogen monoxide introduced into the methyl nitrite-regenerating column of the third step.

13. The process as claimed in claim 1, wherein in the stage (b) of the fifth step, the molecular oxygen-containing gas contains molecular oxygen in amount of 0.2 mole or more per mole of nitrogen monoxide contained in the purge gas.

14. The process as claimed in claim 1, wherein the methyl alcohol fractions containing methyl nitrite and provided in the stages (a) and (b) of the fifth step are recycled to the methyl nitrite-regenerating column for the third step.

15. The process as claimed in claim 1, wherein in the fourth step, the absorbing medium fraction produced in the second step is subjected to an extract-distilling procedure to remove low boiling-temperature compounds and then to a distilling procedure to collect dimethyl carbonate.

16. The process as claimed in claim 1, wherein in the third step, the non-condensed gas is mixed with a $NO_x$ gas.

* * * * *